(12) United States Patent
Shiraishi et al.

(10) Patent No.: US 7,846,475 B2
(45) Date of Patent: Dec. 7, 2010

(54) SOFT CAPSULES

(75) Inventors: Sumihiro Shiraishi, Hiroshima (JP); Yoshiyuki Shimokawa, Hiroshima (JP); Manabu Udayama, Hiroshima (JP)

(73) Assignee: Wakunaga Pharmaceutical Co., Ltd., Osaka-shi (JP)

( * ) Notice: Subject to any disclaimer, the term of this patent is extended or adjusted under 35 U.S.C. 154(b) by 835 days.

(21) Appl. No.: 10/481,892

(22) PCT Filed: Jul. 3, 2002

(86) PCT No.: PCT/JP02/06753

§ 371 (c)(1), (2), (4) Date: Jan. 5, 2004

(87) PCT Pub. No.: WO03/004003

PCT Pub. Date: Jan. 16, 2003

(65) Prior Publication Data

US 2004/0180083 A1    Sep. 16, 2004

(30) Foreign Application Priority Data

Jul. 5, 2001  (JP) .............................. 2001-204870

(51) Int. Cl.
  *A61K 9/48*   (2006.01)
  *A61K 9/66*   (2006.01)
(52) U.S. Cl. ...................... 424/452; 424/455
(58) Field of Classification Search ............. 424/452, 424/455
  See application file for complete search history.

(56) References Cited

U.S. PATENT DOCUMENTS 4,500,453 A * 2/1985 Shank ...................... 530/354
4,701,327 A * 10/1987 Henmi et al. ............... 424/455
5,288,550 A * 2/1994 Sakato ..................... 428/321.5
6,387,417 B1 * 5/2002 Iwai ........................ 424/729
6,458,383 B2 * 10/2002 Chen et al. ................. 424/451

FOREIGN PATENT DOCUMENTS

| JP | 52-35178 | | 3/1977 |
| JP | 56-30915 | | 3/1981 |
| JP | 61207328 A | * | 9/1986 |
| JP | 62-67020 | | 3/1987 |
| JP | 63-164858 | | 7/1988 |
| JP | 64-20078 | * | 1/1989 |
| JP | 01020078 A | * | 1/1989 |
| JP | 1-313421 | | 12/1989 |
| JP | 5-43451 | | 2/1993 |
| JP | 5-310566 | | 11/1993 |
| JP | 2000-344661 | | 12/2000 |
| WO | 93/11753 | | 6/1993 |

* cited by examiner

Primary Examiner—Blessing M Fubara
(74) Attorney, Agent, or Firm—Oblon, Spivak, McClelland, Maier & Neustadt, L.L.P.

(57) ABSTRACT

The present invention provides soft capsules comprising a capsule shell having a water activity lower than that of a capsule filling; and a production process of the soft capsules. The present invention makes it possible to prepare soft capsules without lowering the water activity of an active ingredient of a medicament or the like, which activity varies widely, depending on the active ingredient employed, leading to the provision of the soft capsules having original unimpaired properties or stability, and moreover, palatability and texture.

5 Claims, No Drawings

SOFT CAPSULES

TECHNICAL FIELD

The present invention relates to soft capsules which can be filled with a solution having a high water activity.

BACKGROUND TECHNIQUE

Conventionally, for soft capsules, a shell composed mainly of gelatin and having a plasticizer such as glycerin added thereto has generally been employed. When an aqueous solution of a medicament or the like is filled in a capsule having such a water soluble polymer shell, the transition of water to the shell and swelling or dissolution of the shell due to this water cannot be avoided in the conventional technique. Soft capsules with such a shell are therefore not a product capable of enduring the distribution.

With a view toward filling soft capsules with a water soluble medicament or an aqueous extract of an animal or plant, various techniques have been investigated. For example, reported are a method of causing an aqueous solution of a medicament to adsorb to an excipient or the like, pulverizing it, suspending the powder in a lipophilic substance and then filling soft capsules with the suspension. Specifically the method comprises adding a surfactant to an aqueous solution of a medicament, uniformly mixing with a lipophilic component such as tocopherol acetate and then filling soft capsules with the resulting solution (Japanese Patent Application Laid-Open No. Sho 62-67020, Japanese Patent Application Laid-Open No. Hei 5-310566); a method of emulsifying a water-containing plant extract or the like in a fatty acid glyceride and then filling soft capsules with the resulting emulsion (Japanese Patent Laid-Open No. Sho 52-35178); a method of adding a water soluble polymer such as polyethylene glycol to an aqueous solution of a medicament such as pantethine and then filling the resulting highly viscous mixture to soft capsules (Japanese Patent Laid-Open No. Sho 56-30915); a method of forming soft capsules from a shell having a gelatin sheet and a polysaccharide sheet stacked one after another in order to impart the gelatin shell with water resistance (Japanese Patent Application Laid-Open No. Sho 63-164858), a method of forming capsules by using a shell made of gelatin and alginic acid, and dipping the resulting capsules in a calcium chloride solution to form an acid resistant film on the surface of the capsules (Japanese Patent Laid-Open No. Hei 1-313421), and a method of adding a large amount of edible fibers to the filling of capsules in order to keep its water content and filling the resulting paste in the capsules (Japanese Patent Laid-Open No. 2000-344661).

These capsules are however accompanied with the problem that lowering in the water activity of the capsule filling by adding, to an aqueous solution of the capsule filling, an oily substance, an O/W type emulsifying or suspending agent or a polymer substance to emulsify the aqueous solution or to heighten its viscosity deteriorates the properties, stability and platability of the medicament, or offers a hindrance to their production. In other words, a method of suspending a powdered medicament in a lipophilic substance or emulsifying or uniformly mixing the medicament in a water soluble polymer solution is not preferred, because it causes an rise in the production cost, limits an amount to be filled in a capsule, or sometimes damages the stability of the medicament by the heat applied during the pulverizing step, and moreover, impairs the original taste or smell of a medicament or extract which has placed an importance on its palatability or texture.

The production of soft capsules made of stacked films involves such a problem that it requires special equipment in addition to an ordinarily employed rotary capsule filler. The method of filling capsules with a paste obtained by adding a large amount of edible fibers and saccharides to the filling also has such a defect that an inevitable stress on a feed pump during a capsule filling step becomes the cause of seizure.

Soft capsules having, encapsulated therein, a filling having a water activity of from 0.55 to 0.80 in a capsule shell having a water activity equal to or greater than the above-described value are developed, but problems such as softening of the capsule or adhesion between capsules occur when the capsule filling has a water activity of 0.80 or greater (Japanese Patent Application Laid-Open No. Sho 64-20078).

Accordingly, a demand continues to exist for capsules which can be retained stably even if encapsulated with a water soluble filling having a high water activity.

An object of the present invention is therefore to provide soft capsules which can be filled with an aqueous solution containing an active ingredient while retaining its high water activity without adding thereto an oily substance, O/W emulsifier, a water soluble polymer or the like.

DISCLOSURE OF THE INVENTION

With the foregoing in view, the present inventors have proceeded with an extensive investigation. As a result, it has been found that by adjusting the water activity of a capsule shell to be lower than that of a capsule filling, the capsule filling can be retained in the capsule stably even if it is a water soluble filling having a high water activity, leading to the completion of the present invention.

In the present invention, there are thus provided a soft capsule comprising a capsule shell having a water activity lower than that of a capsule filling; and a production process thereof.

BEST MODE FOR CARRYING OUT THE INVENTION

In the soft capsules of the present invention, the water activity of the capsule shell is lower than that of the capsule filling. Such capsules are utterly unknown hitherto. The term "water activity (a)" as used herein means a ratio ($P/P_0$), at the same temperature, of a water vapor pressure P of a medium containing water to a vapor pressure $P_0$ of pure water and it is a parameter indicating the activity of water in the medium.

There is no particular limitation imposed on the water activity of the filling in the soft capsules of the present invention. A solution having a water activity exceeding 0.80 can be filled, but in consideration of the balance with the water activity of the shell, the water activity is preferably $0.50 \leq a \leq 1$, more preferably $0.65 \leq a \leq 0.95$, especially preferably $0.70 \leq a \leq 0.90$.

No particular limitation is imposed on the properties or appearance of the capsule filling, and in addition to a solution having the filling dissolved therein, an emulsion or suspension of the filling may be used.

The water activity of the capsule shell must be lower than that of the capsule filling, preferably $0.25 \leq a \leq 0.90$, especially $0.40 \leq a \leq 0.70$.

Accordingly, the soft capsules of the present invention are particularly preferred when a capsule shell has a water activity lower than that of the filling and at the same time, the water activity of the filling is $0.50 \leq a \leq 1$ and that of the capsule shell is $0.25 \leq a \leq 0.90$.

In addition, from the viewpoints of long term storage and stability upon distribution, the soft capsules of the present invention are preferred when the transfer of the water content in the capsule shell to the capsule filling or transfer of the water content in the capsule filling to the capsule shell is suppressed by adjusting a ratio of the water content (C) of the capsule filling to the water content (S) of the capsule shell. The C/S ratio is preferably $0.7 \leq C/S \leq 15$, more preferably $1.0 \leq C/S \leq 10$, especially preferably $1.0 \leq C/S \leq 7.0$.

Although no particular limitation is imposed on the kinds of the capsule filling, preferred examples include pharmaceuticals, quasi drugs, cosmetics, health food, food, beverages, seasonings, perfumes and bath agents. More specifically, as well as raw materials for pharmaceuticals, quasi drugs and cosmetics regulated by the Pharmaceutical Affairs Law, any materials which can be used for health foods, foods, beverages or seasonings can be used. Examples include extracts of crude drugs such as mallotus bark, gambir, aloe, epimedii herb, fennel, mume fruit, lindera root, bearberry leaf, curcumae rhizome, rose fruit, *Acanthopanax Sessiliflorus*, corydalis tuber, *Isodon japonicus*, astragalus root, scutellaria root, polygomati rhizome, phellodendron bark, Pruni Jamasakura bark, coptis rhizome, polygala root, Phocae Thstis Et Penis, hippocampus, *Polygonum multiflorum* root, zedoary, pueraria root, Japanese valerian, chamomille, guarana, glycyrrhiza, platycodon root, immature orange, ox bile, apricot kernel, lycii fruit, wormwood, cinnamon bark, cassia seed, gentian, geranium herb, red ginseng, magnolia bark, oriental bezoar, acanthopanacis bark, achyranthes, evodia fruit, schisandra fruit, bupleurum root, asiasarum root, thyme, sage, smilax rhizome, crataegus fruit, gardenia fruit, cornus fruit, zanthoxylum fruit, jujube seed, dioscorea rhizome, rehmannia root, civet, peony root, cnidium fruit, plantago herb, huttuynia herb, amomum seed, ginger, cardamom, ligustrum, lumbricalis, XIN YI, senega, cnidium rhizome, peucedani radix, swertia herb, atractylodes, mori cortex, perillae herba, rhubarb, jujube, clove, Uncariae Uncis Cumramlus, Citrus Unshiu peel, capsicum, Japanese Angelica root, DANG SHEN, cordyceps, persicae semen, bitter orange peel, ipecac, cuscuta seed, eucommia bark, nandina fruit, cornsilk, cistanchis herb, ginseng, garlic, ophiopogon tuber, glehniae radix cum rhizoma, pinellia tuber, Agkistrodon Japonica, atractylodes rhizome, *Poria sclerotium*, sinomenium stem, psoralea seed, moutan bark, hop, ephedra herb, actinidia fruit, *Muira puama*, saussurea root, coix seed, *Longan aril*, Japanese gentian, scopolia rhizome, and hairy antler; extracts of an animal or plant such as brueberry, bilberry, Echinacea, *Chrysanthemum morifolium* Ramat., green barley, carthami flos, Salacia Oblonga, rosemary, honey suckle, Panax Noto ginseng, *Ginkgo biloba*, Artemisia herb, green tea, herbs, mushrooms, and organs of animals such as liver, heart and placenta, and hydrolysates prepared using them with an acid, base or enzyme; extracts of cereals, plants or marine foods fermented with rice koji, red koji, lactic acid bacteria, acetic acid bacteria, Natto bacteria, yeast or the like; water soluble vitamins such as vitamins B1, vitamins B2, niacin, vitamins B6, vitamins B12, pantothenic acid, biotin, folic acid and vitamins C; fat soluble vitamins such as vitamin A, vitamin D, vitamin E and vitamin K; and amino acids, peptides, proteins, nucleic acids, DNA and the like. No particular limitation is imposed on the extracting method of the above-described extract. Generally known methods of extracting with water or hydrous alcohol can be adopted. Alternatively, tinctures, fluid extracts, soft extracts, dry extracts and the like prepared by the method as described in the Japanese Pharmacopoeia can also be employed. Of theses crude drug extracts and animal or plant extracts are particularly preferred because they exist stably as an aqueous solution and can be formulated into capsules without changing this form.

The above-described capsule filling may contain an excipient, pH regulator or the like as needed.

Examples of the excipient include dispersing auxiliaries such as carboxymethyl cellulose, povidone, gum arabic and phospholipids, solubilizing agents such as ethanol, polyoxyethylene hydrogenated castor oil, glycerin fatty acid ester, decaglycerin fatty acid ester and polyglycerin fatty acid ester, colorants such as caramel, flavoring agents, saccharides such as glucose, sucrose, galactose, maltose and xylose, sugar alcohols such as sorbitol, multitol and xylitol, polysaccharides such as pullulan and hydrolysates of a polysaccharide, and components ordinarily employed for liquid preparations. These excipients may be used either singly or in combination.

As the pH regulator, those generally known in the pharmaceutical manufacturing technology are usable. Examples include inorganic acids such as hydrochloric acid, nitric acid, sulfuric acid and phosphoric acid, organic acids such as citric acid, succinic acid, fumaric acid, tartaric acid, lactic acid, malic acid, aspartic acid, and glutamic acid, salts of these inorganic or organic acids, and alkalis such as sodium hydroxide, potassium hydroxide, magnesium hydroxide, calcium hydroxide, sodium bicarbonate, potassium bicarbonate, calcium bicarbonate, sodium carbonate, potassium carbonate and calcium carbonate. They may be used either singly or in combination.

Examples of the material used for the capsule shell include water soluble polymers, for example, peptides including gelatin and gelatin derivatives such as succinated gelatin, gelatin hydrolysate, hydrolyzed gelatin and cross-linked gelatin, polysaccharides such as sodium alginate, pullulan, glucomannan, gum arabic, and carrageenan, and celluloses such as hydroxypropylmethyl cellulose and hydroxypropyl cellulose, and synthetic polymers such as Eudragit and polyvinyl pyrrolidone. Of these, gelatin and succinated gelatin are particularly preferred. It is added in an amount of from 20 to 80 wt. %, preferably from 30 to 70 wt. % based on the total weight of the shell.

In the shell of the soft capsule of the present invention, it is possible to incorporate, as well as auxiliary agents necessary for forming the shell such as water activity lowering agent, humectant, pH regulator and antiseptic, a deposit inhibitor, an oily substance, a substance unstable to water or another active ingredient such as a medicament which may cause an interaction with an active ingredient of the filling as needed, insofar as the above-described water activity or C/S ratio can be attained.

The water activity of the shell can be adjusted to the desired value by the addition of a water activity lowering agent. Such water activity lowering agents include monosaccharides or disaccharides such as glucose, sucrose, galactose, maltose and xylose, amino acids and derivatives thereof such as glycine, serine, and trimethylglycine, sugar alcohols such as sorbitol and multitol, salts such as magnesium chloride, magnesium sulfate, ammonium chloride, sodium acetate and sodium chloride, organic acids such as citric acid and malic acid, alcohols such as ethanol and glycerin. One or more of them may be added in the shell. By adding a humectant, the water content of the capsule shell after drying can be kept at a fixed level, making it possible to retain the shape of the capsule for long hours. Such humectants include sugar alcohols such as glycerin, sorbitol, erythritol, mannitol, xylitol and trehalose, polysaccharides such as pullulan, and hydrolysates of the polysaccharide. One or more than one of them may be incorporated in the shell. In this case, it is preferred to add the humectant to the shell material so that a ratio of the shell material to the humectant ranges from 1:2 to 3:1, especially from 1:1 to 3:1.

As the pH regulator for controlling the pH of the shell, acids or bases generally known in the pharmaceutical manufacturing technology can be used. Examples include inorganic acids such as hydrochloric acid, nitric acid, sulfuric acid and phosphoric acid, organic acids such as citric acid, fumaric acid, tartaric acid, lactic acid, malic acid, aspartic acid and glutamic acid, salts of these acids, and bases such as sodium hydroxide, potassium hydroxide, magnesium hydroxide, calcium hydroxide, sodium bicarbonate, potassium bicarbonate, calcium bicarbonate, sodium carbonate, potassium carbonate, and calcium carbonate. They may be used either singly or in combination.

Examples of the deposit inhibitor include starch, carnauba wax and magnesium stearate. They may be used either singly or in combination.

The soft capsules of the present invention can be coated with an ordinarily employed coating agent. Examples include hydroxypropylmethyl cellulose, ethyl cellulose, Eudragits and shellac. They may be used either singly or in combination.

Medicaments causing an interaction with the active ingredient of the filling (for example, vitamin B12 and vitamin C, thiamine hydrochloride and nicotinic acid amide, folic acid and riboflavin) may be incorporated in the capsule shell and capsule filling, respectively. A substance which has a problem in stability in an aqueous solution (vitamins, for example, vitamins B1, vitamins B2, niacin, vitamins B6, vitamins B12, pantothenic acid, biotin, folic acids and vitamins C) are preferably incorporated in the capsule shell.

The soft capsules of the present invention can be produced in accordance with the conventional soft capsule producing method by filling a capsule filling in a capsule shell, forming into capsules and then drying them. Specific examples of the method include a stamping method using a rotary full-automatic soft capsule forming machine; a plate method of inserting the filling between two gelatin sheets, pressing molds on both sides against the sheets, and then stamping, and a drip method (seamless capsule) by using a double nozzle. The water activity and water content may be adjusted individually for the capsule filling and capsule shell prior to the formation into capsules or may be adjusted by controlling the drying conditions (for example, drying temperature, relative humidity at the time of drying and drying time) properly to lower the water content of the capsule shell after the formation into capsules, or by using these two methods in combination.

The soft capsules of the present invention can be packaged in the generally known form, for example, bottle package, aluminum packaging and PTP packaging. Of these, PTP packaging is particularly preferred.

In the preferred mode, the soft capsules of the present invention are oval #5 soft capsules; have, as a capsule filling, a crude drug extract having a water activity of $0.70<a<0.96$; have, as a capsule shell material, a peptide such as gelatin having a water activity of $0.40 \leqq a \leqq 0.70$; contain, in their shell, a sugar alcohol such as glycerin or sorbitol as humectant and a vitamin such as vitamins B1 or vitamins B12; and have a C/S ratio falling within a range of from 1.0 to 10.0.

EXAMPLES

The present invention will hereinafter be described in further detail by Examples. It should however be borne in mind that the present invention is not limited to or by them.

Example 1

Preparation of Soft Capsules

After 45 wt. % of gelatin, 15 wt. % of glycerin and 40 wt. % of water were dissolved at 70° C. and the resulting gelatin solution was defoamed, it was allowed to stand at 60° C. for about 10 hours, whereby a gelatin solution having a water activity (a) of 0.88 was obtained. By using a rotary soft capsule filler (oval #5), each of ginseng extracts different in water activity (water activity (a): 0.84 and 0.94) was filled in capsules made from the gelatin solution. After formation, the resulting capsules were dried at 27° C. and a humidity of 50% or less. Some capsules were sampled at a proper time. After confirmation that the water activity in the capsule shell was smaller than that of the capsule filling, soft capsules as shown in Table 1 were prepared. The water activity of each of the shell and filling was determined by weighing the capsule just after sampling, taking out the filling, washing the shell with hexane and then measuring the water activity of them by a water activity measuring apparatus ("AW-Wert-Messer; manufactured by Duratherm). In addition, based on the drying loss and initial water content (S) in the shell, a ratio (C/S) of the water content (C) of the filling to S was calculated.

TABLE 1

| | Water activity (a) of gelatin solution: 0.88 | | | | | |
|---|---|---|---|---|---|---|
| No. | Water activity of ginseng extract | Amount filled (mg) | Drying time (hrs) | Water activity of capsule shell | Water activity of capsule filling | C/S |
| 1 | 0.84 | 250 | 24 | 0.75 | 0.81 | 0.7 |
| 2 | 0.84 | 300 | 36 | 0.72 | 0.83 | 1.3 |
| 3 | 0.84 | 400 | 48 | 0.65 | 0.82 | 5.9 |
| 4 | 0.94 | 300 | 60 | 0.63 | 0.88 | 7.9 |
| 5 | 0.94 | 300 | 72 | 0.60 | 0.88 | 9.1 |
| 6 | 0.94 | 350 | 84 | 0.58 | 0.89 | 11.1 |
| 7 | 0.94 | 400 | 108 | 0.44 | 0.90 | 14.3 |
| 8 | 0.84 | 200 | 108 | 0.40 | 0.76 | 3.6 |

The soft capsules thus prepared were packaged in PTP. After storage at 25° C. and 60% RH for 6 months, existence of leakage of the filling was studied. Observation results of the change are shown in Table 2. Neither leakage of the filling from these soft capsules nor their deformation was recognized after storage at 25° C. and 60% RH.

TABLE 2

| No. | After storage for 2 months | | After storage for 4 months | | After storage for 6 months | |
|---|---|---|---|---|---|---|
| | Leakage | Deformation | Leakage | Deformation | Leakage | Deformation |
| 1 | ○ | — | ○ | — | ○ | — |
| 2 | ○ | — | ○ | — | ○ | — |
| 3 | ○ | — | ○ | — | ○ | — |
| 4 | ○ | — | ○ | — | ○ | — |
| 5 | ○ | — | ○ | — | ○ | — |
| 6 | ○ | — | ○ | — | ○ | — |
| 7 | ○ | — | ○ | — | ○ | — |
| 8 | ○ | — | ○ | — | ○ | — |

○: No leakage was observed.
—: No deformation

Example 2
Preparation of Soft Capsules

After 25 wt. % of gelatin, 50 wt. % of glycerin and 25 wt. % of water were dissolved at 70° C. and the resulting gelatin solution was defoamed, two gelatin sheets (water activity (a): 0.81) of about 1 mm in thickness were prepared using a flattening plate. Over one of the gelatin sheets laid on a bottom force, each of ginseng extracts different in water activity (water activity (a): 0.85, 0.90 and 0.94) was cast, followed by stacking a top force having the other gelatin sheet laid thereover. These top and bottom forces were compressed by a compressor to form soft capsules. These soft capsules were dried at 25° C. and a humidity of 50% or less. Some capsules were sampled at a proper time. After conformation that the water activity in the capsule shell was smaller than that of the capsule filling, soft capsules as shown in Table 3 were prepared. The soft capsules were weighed just after sampling and the filling was taken out therefrom. Then, the water activity, drying loss and water content were measured as in Example 1. The soft capsules thus prepared are shown in Table 3.

TABLE 3

Water activity (a) of gelatin sheet: 0.81

| No. | Water activity of ginseng extract | Amount filled (mg) | Drying time (hrs) | Water activity of capsule shell | Water activity of capsule filling | C/S |
|---|---|---|---|---|---|---|
| 1 | 0.85 | 210 | 16 | 0.74 | 0.84 | 0.8 |
| 2 | 0.90 | 240 | 24 | 0.73 | 0.86 | 2.2 |
| 3 | 0.90 | 270 | 36 | 0.64 | 0.85 | 4.1 |
| 4 | 0.94 | 280 | 60 | 0.52 | 0.89 | 8.1 |
| 5 | 0.94 | 330 | 72 | 0.43 | 0.88 | 13.2 |

The soft capsules thus prepared were charged in a glass bottle. After storage at 35° C. and 25° C., respectively, existence of leakage of the filling was studied. Observation results of a change in the shape are shown in Tables 4 and 5. Neither leakage of the filling from these soft capsules nor their deformation was recognized after respective storage at 35° C. and 25° C.

TABLE 4

| | Storage at 35° C. | | | |
|---|---|---|---|---|
| | After storage for 2 months | | After storage for 4 months | |
| No. | Leakage | Deformation | Leakage | Deformation |
| 1 | ○ | — | ○ | — |
| 2 | ○ | — | ○ | — |
| 3 | ○ | — | ○ | — |
| 4 | ○ | — | ○ | — |
| 5 | ○ | — | ○ | — |

○: No leakage was observed.
—: No deformation

TABLE 5

| | Storage at 25° C. | | | |
|---|---|---|---|---|
| | After storage for 2 months | | After storage for 4 months | |
| No. | Leakage | Deformation | Leakage | Deformation |
| 1 | ○ | — | ○ | — |
| 2 | ○ | — | ○ | — |
| 3 | ○ | — | ○ | — |
| 4 | ○ | — | ○ | — |
| 5 | ○ | — | ○ | — |

○: No leakage was observed.
—: No deformation

Example 3

In an emulsifying machine, 45 kg of succinated gelatin, 15 kg of glycerin and 40 kg of water were charged and succinated gelatin was dissolved by stirring at 70° C. After the resulting solution was defoamed under reduced pressure, it was allowed to stand at 60° C. for 10 hours to prepare a succinated gelatin solution (water activity (a): 0.87) for shell was prepared. By using a rotary soft capsule filler (oval #5), 250 mg or 350 mg per capsule of a garlic extract (water activity (a): 0.88) was filled. After formation, drying was performed for from 4 to 6 days at 27° C. and a humidity of 50% or less, whereby two types of soft capsules were prepared (1: amount filled: 250 mg, water activity (a) of shell: 0.53, water activity (a) of filling: 0.77 and C/S: 1.50; 2: amount filled: 350 mg, water activity (a) of shell: 0.54, water activity (a) of filling: 0.82 and C/S: 3.50). After these two types of soft capsules were subjected to glass-bottle packaging or PTP packaging and stored at 35° C., existence of the leakage of the filling, deformation, and disintegration time were studied and results are shown in Table 6. They were found to be almost free from leakage of the filling, deformation of the capsule and delay in disintegration time.

TABLE 6

| No. | Packaging | What is evaluated | Storage for 1 month | Storage for 2 months |
|---|---|---|---|---|
| 1: 250 mg of the extract was filled (shell (a): 0.53) (filling (a): 0.77) (C/S: 1.50) | PTP packaging | Leakage of filling<br>Deformation<br>Disintegration time (initial value: 5.5 min) | Not observed<br>Not observed<br>6.0 min. | Not observed<br>Not observed<br>6.0 min. |
| | Glass bottle packaging | Leakage of filling<br>Deformation<br>Disintegration time (initial value: 5.5 min) | Not observed<br>Not observed<br>6.0 min. | Not observed<br>Not observed<br>6.5 min. |
| 2: 350 mg of the extract was filled (shell (a): 0.54) (filling (a): 0.82) (C/S: 3.50) | PTP packaging | Leakage of filling<br>Deformation<br>Disintegration time (initial value: 6.0 min) | Not observed<br>Not observed<br>6.5 min. | Not observed<br>Not observed<br>6.5 min. |
| | Glass bottle packaging | Leakage of filling<br>Deformation<br>Disintegration time (initial value: 6.0 min) | Not observed<br>Not observed<br>7.0 min. | Not observed<br>Not observed<br>6.5 min. |

Example 4

In an emulsifying machine, 33 kg of succinated gelatin, 24 kg of glycerin and 33 kg of water were charged and succinated gelatin was dissolved by stirring at 70° C. After the resulting solution was defoamed under reduced pressure, it was allowed to stand at 60° C. for about 10 hours to prepare a succinated gelatin solution (water activity (a): 0.85) for shell. By using a rotary soft capsule filler (oval #5), 150 mg, 250 mg or 350 mg per capsule of a garlic extract (water activity (a): 0.92) was filled. After formation, drying was performed for 5 to 7 days at 25° C. and a humidity of 40% or less, whereby three types of soft capsules were prepared (1: amount filled: 150 mg, water activity (a) of shell: 0.57, water activity (a) of filling: 0.78 and C/S: 1.25; 2: amount filled: 250 mg, water activity (a) of shell: 0.54, water activity (a) of filling: 0.76 and C/S: 2.35; 3: amount filled: 350 mg, water activity (a) of capsule shell: 0.55, water activity (a) of filling: 0.83, C/S: 3.52). These three types of soft capsules were subjected to glass bottle packaging or PTP packaging, stored at 35° C. and existence of the leakage of the filling, deformation, and disintegration time were studied and results are shown in Table 7. They were found to be almost free from leakage of the filling, deformation of the capsule and delay in disintegration time.

TABLE 7

| No. | Packaging | What is evaluated | Storage for 1 month | Storage for 2 months |
|---|---|---|---|---|
| 1: 150 mg of the extract was filled (shell (a): 0.57) (filling (a): 0.78) (C/S: 1.25) | PTP packaging | Leakage of filling<br>Deformation<br>Disintegration time (initial value: 6.0 min) | Not observed<br>Not observed<br>6.0 min. | Not observed<br>Not observed<br>6.5 min. |
| | Glass bottle packaging | Leakage of filling<br>Deformation<br>Disintegration time (initial value: 6.0 min) | Not observed<br>Not observed<br>6.5 min. | Not observed<br>Not observed<br>6.5 min. |
| 2: 250 mg of the extract was filled (shell (a): 0.54) (filling (a): 0.76) (C/S: 2.35) | PTP packaging | Leakage of filling<br>Deformation<br>Disintegration time (initial value: 6.5 min) | Not observed<br>Not observed<br>7.5 min. | Not observed<br>Not observed<br>7.0 min. |
| | Glass bottle packaging | Leakage of filling<br>Deformation<br>Disintegration time (initial value: 6.5 min) | Not observed<br>Not observed<br>7.0 min. | Not observed<br>Not observed<br>6.5 min. |
| 3: 350 mg of the extract was filled (shell (a): 0.55) (filling (a): 0.83) (C/S: 3.52) | PTP packaging | Leakage of filling<br>Deformation<br>Disintegration time (initial value: 6.5 min) | Not observed<br>Not observed<br>7.0 min. | Not observed<br>Not observed<br>7.0 min. |
| | Glass bottle packaging | Leakage of filling<br>Deformation<br>Disintegration time (initial value: 6.5 min) | Not observed<br>Not observed<br>7.5 min. | Not observed<br>Not observed<br>7.5 min. |

Example 5

In an emulsifying machine, 28 kg of succinated gelatin, 20 kg of glycerin, 0.2 g of cyanocobalamin and 28 kg of water were charged and succinated gelatin was dissolved by stirring at 70° C. After the resulting solution was defoamed under reduced pressure, it was allowed to stand at 60° C. for about 10 hours to prepare a succinated gelatin solution (water activity (a): 0.86) for shell. By using a rotary soft capsule filler (oval #4), 260 mg per capsule of a garlic extract (water activity (a): 0.92) was filled. After formation, drying was performed for 5 days at 25° C. and a humidity of 40% or less, whereby soft capsules were prepared (water activity (a) of shell: 0.52, water activity (a) of filling: 0.82 and C/S: 2.90).

The soft capsules were subjected to glass bottle packaging or PTP packaging, stored at 35° C. and existence of the leakage of the filling, deformation of the capsule, disintegration time and stability of Vitamin were studied and results are shown in Table 8. They were found to be almost free from reduction in the content of cyanocobalamin, leakage of the filling, deformation of the capsule and delay in disintegration time.

TABLE 8

| Packaging | What is evaluated | Storage for 1 month | Storage for 2 months |
|---|---|---|---|
| PTP packaging | Content of cyanocobalamin (relative to the initial value) | 99.2% | 98.9% |
| | Disintegration time (initial value: 7.0 min) | 7.5 min | 7.5 min |
| | Leakage of filling | Not observed | Not observed |
| | Deformation of capsule | Not observed | Not observed |
| Glass bottle packaging | Content of cyanocobalamin (relative to the initial value) | 99.3% | 99.0% |
| | Disintegration time (initial value: 7.0 min) | 7.0 min | 8.0 min |
| | Leakage of filling | Not observed | Not observed |
| | Deformation of capsule | Not observed | Not observed |

INDUSTRIAL APPLICABILITY

The present invention makes it possible to prepare soft capsules while retaining a high water activity of the filling, and therefore to provide soft capsules of a medicament or the like having original unimpaired properties or stability, and moreover palatability and texture.

The invention claimed is:

1. A soft capsule comprising a capsule shell having a water content (S) and a capsule filling having a water content (C) which is a crude drug extract in aqueous solution, an animal extract in the form of an aqueous solution or a plant extract in the form of an aqueous solution, wherein a solution for the capsule shell comprises a shell material and a humectant or water activity lowering agent, wherein the shell material comprises gelatin, a gelatin derivative, a polysaccharide, a cellulose, or a synthetic polymer,
wherein said gelatin derivative is at least one selected from the group consisting of succinated gelatin, hydrolyzed gelatin, and cross-linked gelatin,
a ratio of the shell material to the humectant or the water lowering agent ranges from 1:2 to 3:1,
a water activity of the capsule filling is $0.5 \leq a \leq 1$ and a water activity of the capsule shell is $0.25 \leq a \leq 0.9$, and
the capsule shell after drying said capsule has the water activity lower than that of the capsule filling, and a ratio of the water content (C) of the capsule filling to the water content (S) of the capsule shell is $0.7 \leq C/S \leq 15$.

2. The soft capsule of claim 1, wherein the capsule shell comprises an active ingredient different from that contained in the capsule filling.

3. A method of producing a soft capsule as claimed in claim 1, the method comprising filling the capsule filling in the capsule shell, and then drying the capsule.

4. The soft capsule of claim 1, wherein
said polysaccharide is at least one selected from the group consisting of sodium alginate, pullulan, glucomannan, gum arabic, and carrageenan,
said cellulose is hydroxypropylmethyl cellulose or hydroxypropyl cellulose, and
said synthetic polymer is an acrylic and methacrylic acid polymer and/or an acrylic and methacrylic acid co-polymer or polyvinyl pirrolidone.

5. The soft capsule of claim 1, wherein the humectant or the water activity lowering agent is glycerin and/or at least one sugar alcohol selected from the group consisting of sorbitol, erythritol, mannitol, xylitol, and trehalose.

* * * * *